(12) United States Patent
Archibald et al.

(10) Patent No.: US 6,576,906 B1
(45) Date of Patent: Jun. 10, 2003

(54) METHOD AND APPARATUS FOR SCREENING COMBINATORIAL LIBRARIES FOR SEMICONDUCTING PROPERTIES

(75) Inventors: William B. Archibald, Hillsborough, CA (US); Marc Hornbostel, Palo Alto, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 0 days.

(21) Appl. No.: 09/414,615

(22) Filed: Oct. 8, 1999

(51) Int. Cl.[7] ............................ G01J 5/02; G01N 33/53; G01N 31/10; G01N 33/543; C01F 17/00
(52) U.S. Cl. ............................ 250/341.4; 250/341.8; 252/62.51; 423/263; 435/7.1; 435/7.2; 435/DIG. 9; 435/DIG. 10; 435/DIG. 11; 435/DIG. 12; 435/DIG. 13; 436/37; 436/501; 436/518
(58) Field of Search ............ 252/62.51; 423/263; 435/7.1, 7.2, DIG. 9–13; 436/501, 518, 37; 250/341.4, 341.8

(56) References Cited

U.S. PATENT DOCUMENTS

| | | | |
|---|---|---|---|
| 5,347,157 A | * | 9/1994 | Hung et al. |
| 5,776,359 A | | 7/1998 | Schultz et al. ............ 252/62.51 |
| 6,045,671 A | | 4/2000 | Wu et al. |
| 6,063,633 A | | 5/2000 | Willson, III |
| 6,151,123 A | | 11/2000 | Nielsen |
| 6,157,449 A | | 12/2000 | Hajduk |
| 6,187,164 B1 | | 2/2001 | Warren et al. |
| 6,203,724 B1 | | 3/2001 | Reiffenrath et al. |
| 6,333,196 B1 | | 12/2001 | Willson, III |

FOREIGN PATENT DOCUMENTS

| | | | |
|---|---|---|---|
| WO | WO 96/11878 | 4/1996 | ............ C01G/51/04 |
| WO | WO 97/32208 | 9/1997 | ............ G01N/31/10 |
| WO | WO 98/03521 | 1/1998 | ............ C07F/19/00 |
| WO | WO 98/15805 | 4/1998 | ............ G01J/4/00 |
| WO | WO 98/15813 | 4/1998 | ............ G01N/21/35 |
| WO | WO 99/07358 | 2/1999 | |
| WO | WO 00/36399 | 6/2000 | ............ G01N/21/25 |

OTHER PUBLICATIONS

Copending U.S. Application No. 09/210,485, filed Dec. 11, 1998.

Copending U.S. Application No. 08/946,135, filed Oct. 7, 1997.

Copending U.S. Application No. 08/941,170, filed Sep. 30, 1997.

C. Kittel, Introduction to Solid State Physics at 142, 214 (6th ed. 1986).

C. Kittel, Introduction to Solid State Physics, 291–315 (6th ed. 1986).

R. Sehr and L. R. Testardi, The Optical Properties of p–Type $Bi_2Te_3$—$Sb_2Te_3$ Alloys between 2—15 microns, 23 J. Phys. Chem. Solids 1219, 1220–22 (1962).

T. Tritt, 478 Materials Research Society Symposium Proceedings at 34 (1997).

W.H. Press et al., Numerical Recipes in C, 584–91 (2d ed. 1997).

* cited by examiner

*Primary Examiner*—Maurie Baker

(57) ABSTRACT

This invention discloses methods, materials, and devices for making and screening combinatorial libraries to identify semi-conducting and thermoelectric materials. The disclosed method includes preparing a combinatorial library of materials, and identifying library members that are semiconductors. The method may include determining a thermoelectric figure of merit, ZT, for each member of a second combinatorial library of materials. The method determines ZT by applying an oscillatory voltage across the library members, measuring power dissipated by library members, and calculating ZT from the power dissipated. The method may also include isolating single-phase materials of the semiconducting library members. The present invention also discloses an apparatus for discovering thermoelectric materials using combinatorial techniques. The apparatus includes a first combinatorial library of materials comprised of thin films arrayed on a substrate, and a device for identifying semiconducting members of the first combinatorial library. In addition, the apparatus may include a device for measuring ZT—a voltage source for applying an oscillatory electrical potential across members of a second combinatorial library arrayed on a substrate, and a device for measuring the resulting power dissipated by library members. The apparatus may also include a device for isolating single-phase materials of library members that were identified as semiconductors.

6 Claims, 9 Drawing Sheets

METHOD AND APPARATUS FOR SCREENING COMBINATORIAL LIBRARIES FOR SEMICONDUCTING PROPERTIES

This application claims priority to international application PCT/US99/07358, filed Apr. 1, 1999, pending. Each of the foregoing applications is incorporated herein by reference in its entirety and are listed as follows: U.S. patent application Ser. No. 09/227,558, filed Jan. 8, 1999, which is a continuation-in-part of U.S. patent application Ser. No. Ser. No. 08/898,715, filed Jul. 22, 1997, and U.S. Provisional Application Nos. Ser. No. 60/050,949, filed Jun. 13, 1997; Ser. No. 60/028,106, filed Oct. 9, 1996; Ser. No. 60/029,255, filed Oct. 25, 1996; Ser. No. 60/035,366, filed Jan. 10, 1997; Ser. No. 60/048,987, filed Jun. 9, 1997; 60/028,105, filed Oct. 9, 1996; and Ser. No. 60/035,202, filed Jan. 10, 1997.

This invention was made in part with government funds under contract no. N00014-98-C-0288. The government has certain rights in this invention.

BACKGROUND OF THE INVENTION

1. Field of the Invention

This invention relates to systems for discovering semi-conducting materials, and more particularly, to methods, materials, and devices for making and screening combinatorial libraries to identify thermoelectric materials.

2. Discussion

In its simplest form, a thermoelectric device comprises a thermoelectric material—usually a semiconductor—sandwiched between a pair of contacts. When an electrical potential is applied between the pair of contacts, heat flows from one contact to the other through the thermoelectric material. This phenomenon, which is called the Peltier effect, occurs whenever direct current flows through a junction between two dissimilar materials. Similarly, when a temperature difference is applied between the pair of contacts, an electrical potential develops which varies continuously from one contact to the other through the thermoelectric material. This latter phenomenon is called the Seebeck effect. Its size depends on the magnitude of the temperature difference, and like the Peltier effect, on the properties of the thermoelectric materials.

Thermoelectric devices exploit the Seebeck effect and the Peltier effect to generate power and to pump heat and they exhibit certain advantages over conventional compressor-based systems. For example, engineers employ thermoelectric devices to cool small volumes, such as portable food and beverage containers, medical devices, and integrated circuits, which would be impractical to cool with bulky conventional refrigeration systems. Furthermore, thermoelectric heat pumps offer greater flexibility than compressor-based refrigeration systems since thermoelectric devices can heat, as well as cool, by simply reversing the direction of electrical current through the device. Moreover, because thermoelectric devices have no moving parts, they generate power quietly and reliably. Despite these advantages, thermoelectric devices are not used for general purpose cooling or for power generation because they are less efficient than compressor-based systems. Indeed, the most efficient thermoelectric power generators currently operate at about 10% Carnot efficiency, whereas conventional compressor-based systems operate at about 30%, depending on the size of the system.

Since efficiency and performance of thermoelectric power generators and heat pumps depend primarily on the properties of the materials used in the device, researchers continue to search for new, better performing thermoelectric materials. But, progress has been slow. Indeed, Bi-Sb-Te alloys remain the most efficient room temperature thermoelectric materials available, though they were first used in thermoelectric devices more than thirty years ago.

The slow pace of discovery is due, in part, to the time and expense of synthesizing and testing thermoelectric materials using conventional techniques. In traditional material science, researchers synthesize a few grams of a candidate material that they test or screen to decide whether it warrants further study. For thermoelectric materials, synthesis involves a labor- and time-intensive alloying process. Since material properties often depend on synthesis conditions, the discovery process usually includes a lengthy search for optimum heating and quenching cycles. In many cases, dopants are added to control microstructure, which further increases complexity of the discovery process. Although in recent years scientists have acquired a better understanding of how material structure and carrier concentration influence thermoelectric variables such as thermoelectric power, thermal conductivity, and electrical resistivity, discovery efforts continue to rely heavily on experiment.

Combinatorial chemistry is one approach for accelerating the discovery of new thermoelectric materials. It is a powerful research strategy when used to discover materials whose properties, as with thermoelectric compositions, depend on many factors. Researchers in the pharmaceutical industry have successfully used such techniques to dramatically increase the speed of drug discovery. Material scientists have employed combinatorial methods to develop novel high temperature superconductors, magnetoresistive materials, phosphors, and catalysts. See, for example, co-pending U.S. patent application "The Combinatorial Synthesis of Novel Materials," Ser. No. 08/327,513 (a version of which is published as WO 96/11878), and co-pending U.S. patent application "Combinatorial Synthesis and Analysis of Organometallic Compounds and Catalysts," Ser. No. 08/898,715 (published as WO 98/03521), which are both herein incorporated by reference.

The use of combinatorial materials science should enable researchers to undertake an efficient, systematic and comprehensive search of new semi-conducting or new thermoelectric materials without many of the problems associated with traditional materials development.

SUMMARY OF THE INVENTION

The present invention generally provides a method for discovering semi-conducting or thermoelectric materials using combinatorial techniques. The method includes preparing a combinatorial library of materials, and identifying library members that are semiconductors. The method selects library members that are semiconductors because, currently, the most efficient room temperature thermoelectric materials are narrow band gap semiconductors. Nonetheless, this invention is generally useful for researching for semi-conducting materials, despite this specification focusing on thermoelectric materials. The combinatorial library is typically prepared by depositing library members on a substrate using physical vapor deposition (PVD) or sol-gel or liquid dispensing techniques. Useful PVD techniques include pulsed laser deposition, magnetron sputtering, thermal evaporation and co-deposition.

Identification of semiconductors includes exposing members to radiation of varying wavelength, and measuring reflectance, or reflectance and transmittance, of incident radiation. The radiation may be from the infrared, visible or ultraviolet ranges, depending on the band gap for the semiconductor that is being researched. For thermoelectric materials, infrared radiation is useful for reflectance and transmittance measurements, with the method determining an optical band gap of each of the library members: the method selects as semiconductors library members having band gaps in the range of about 0.05 eV to about 0.9 eV (30 microns to about 1 micron). Alternatively, identification may include determining, from reflectance and transmittance measurements, ratios of charge carrier density to quasiparticle effective mass of the library members. If transmittance measurements are not available, e.g., as in the case of an IR opaque substrate, the method uses reflectance measurements alone to identify library members that are semiconductors. For example, the method includes selecting members of the combinatorial library of materials exhibiting reflectance versus incident IR energy (wavelength) curves that are characteristic of a semiconductor. Such curves generally exhibit a local minimum in reflectance.

Alternatively, or in addition to identifying semiconductors, the method may include determining a thermoelectric figure of merit, ZT, for each member of a combinatorial library of materials. To determine ZT, the method includes applying an oscillatory voltage, having a reference frequency $\omega_0$, across each library member, measuring power dissipated by the library members while the oscillatory voltage is applied, and calculating ZT from the power dissipated. The method calculates ZT from the ratio $P(\omega_0)/P(2\omega_0)$, where $P(\omega_0)$ and $P(2\omega_0)$ are, respectively, amplitudes of the power at the reference frequency and at two times the reference frequency. The method can use various techniques to measure the power dissipated, including monitoring infrared emission from each of the library members during application of the oscillatory voltage.

When the method includes identification of library members that are semiconductors and subsequent determination of ZT, the method usually includes isolating single-phase materials of the semiconducting library members. Isolation of single-phase materials may include determining the number of phases present in each of the semiconducting library members, and/or identifying compositions of the phases. The method can use various techniques to determine the number and/or composition of phases, including differential scanning calorimetry, x-ray diffraction, energy dispersive x-ray spectroscopy, secondary ion mass spectroscopy, x-ray fluorescence spectroscopy, and the like.

In addition, the present invention generally provides an apparatus for discovering semi-conducting or thermoelectric materials using combinatorial techniques. The apparatus includes a combinatorial library of materials comprised of thin films arrayed on a substrate, and a device for identifying semiconducting members of the combinatorial library of materials. The substrate can be transparent or opaque to the radiation of interest, and may comprise multiple layers. For example, an infrared transparent substrate may comprise an IR transparent membrane disposed on a support layer, with the membrane interposed between the thin films and the support layer. The support layer may have apertures aligned with the thin films that allow transmission of IR radiation through an otherwise IR opaque support layer. Similarly, an IR opaque substrate may comprise an infrared reflective layer disposed on a support layer, the infrared reflective layer interposed between the thin films and the support layer. Useful devices for identifying semiconductors include an FTIR spectrometer, which can be outfitted with a computer-controlled stage for positioning the thin films arrayed on the substrate.

Alternatively, or in addition to the device for identifying semiconductors, the apparatus may include a device for measuring ZT: a voltage source for applying an oscillatory electrical potential across members of a combinatorial library arrayed on a substrate, and a device for measuring power dissipated by each of the library members during application of the oscillatory electrical potential. The members of the combinatorial library are generally arrayed on a substrate having a lower or comparable thermal conductivity than the library members and each of the library members are typically connected, in parallel, to the voltage source. Useful devices for measuring power dissipated by each of the library members include infrared detectors, such as bolometers, photodiodes, focal plane arrays, thermcouples, thermistors, resistance thermometric devices, and the like. The apparatus may also include a computer for transforming power from the time domain to the frequency domain, and a vacuum chamber for containing the library during application of the oscillatory electrical potential.

When the apparatus includes devices for identification of semiconducting library members and for subsequent determination of ZT, the apparatus usually includes a device for isolating single-phase materials of library members that were identified as semiconductors. Devices for isolating single-phase materials include a differential scanning calorimeter, a scanning x-ray diffraction unit, an energy dispersive x-ray spectrometer, a secondary ion mass spectrometer, an x-ray fluorescence spectrometer, and the like.

DETAILED DESCRIPTION OF THE PREFERRED EMBODIMENTS

The present invention will be discussed in terms of researching, discovering or optimizing thermoelectric materials. However, those of skill in the art will understand that because semi-conducting measurements are being made, the method and apparatus herein is generally useful for any semi-conducting materials.

The dimensionless thermoelectric figure of merit, ZT, provides a measure of the efficiency of a thermoelectric device operating at temperature T(K), and is defined by equation I:

$$ZT \equiv \frac{S^2 T}{\rho K} \qquad \text{I}$$

In equation I, S, $\rho$, and K are, respectively, Seebeck coefficient ($VK^{-1}$), resistivity ($\Omega$ cm), and thermal conductivity ($Wcm^{-1}K^{-1}$) of a material in the thermoelectric device. Larger ZT corresponds to higher device efficiency. The methods, materials, and devices described below focus on maximizing ZT using combinatorial synthesis and screening techniques.

Overview of Method

Figure 1:
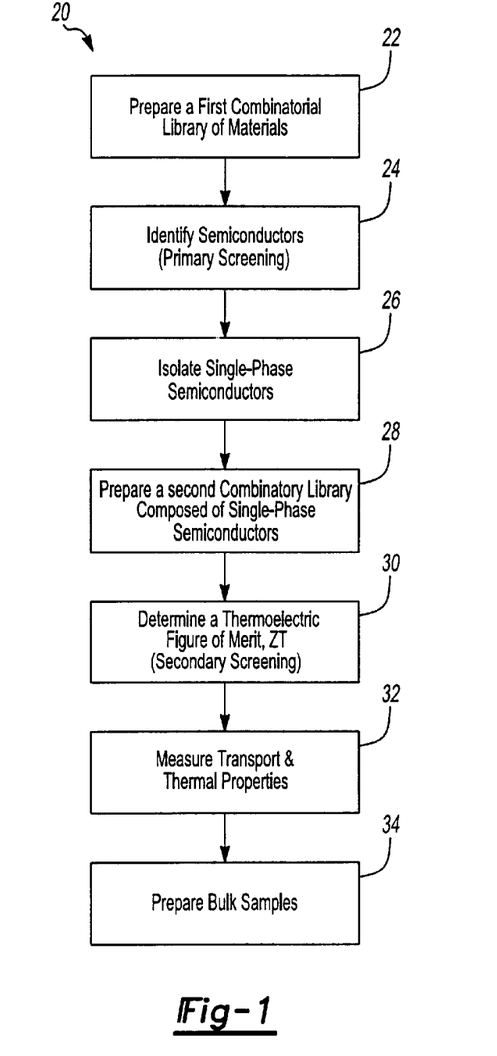
FIG. 1 illustrates general features of a method for discovering semi-conducting or thermoelectric materials.

FIG. 1 illustrates general features of a method 20 for discovering semi-conducting or thermoelectric materials. The method 20 includes preparing 22 candidate materials using combinatorial methods. These materials—which comprise a first combinatorial library—typically span a broad range of compositions and may include hundreds of individual samples or library members. To focus discovery efforts, the library members undergo testing or primary screening 24 to identify a subset of the most promising materials, which are then evaluated in subsequent steps of the method 20. Currently, the most efficient room temperature thermoelectric materials are narrow band gap semiconductors, such as $Bi_2Te_3$. For this reason, primary screening 24 eliminates library members that are not semiconductors. Since primary screening 24 does not distinguish between single-phase and multiple-phase semiconductors, the method 20 includes isolating 26 single-phase semiconductors from among library members identified by primary screening 24. The isolating step 26 is included in the method 20 because a phase exhibiting a low ZT in a multiphase material can mask another phase exhibiting a higher ZT.

As shown in FIG. 1, the method 20 also includes preparing 28 a second combinatorial library that comprises at least a portion of the single-phase materials from the isolating step 26. Next, the method 20 determines the thermoelectric figure of merit, or a quantity related to ZT, of each member of the second combinatorial library. Secondary screening 30, identifies a subset of library members with largest ZT, and presumably, highest thermoelectric performance. If desired, this subset of library members may undergo further testing 32 to determine S, $\rho$, and k or other material properties. In addition, the method 20 may also include making 34 bulk samples of one or more members of the first or second combinatorial libraries using conventional techniques. One may then measure ZT, S, $\rho$, K or other material properties of the bulk samples to verify results of primary 24 and secondary 30 screening.

Preparation of a First Combinatorial Library of Materials

Figure 2:
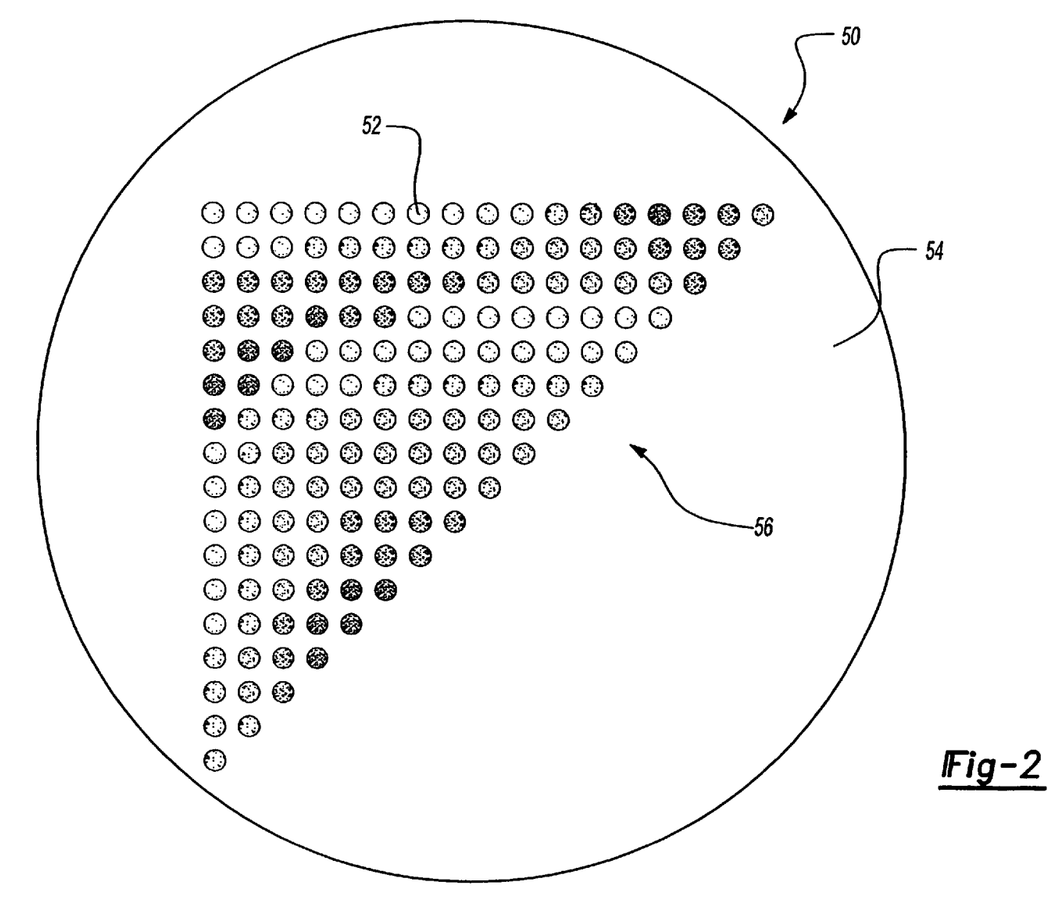
FIG. 2 depicts a typical first combinatorial library, which is comprised of discrete thin films arrayed on a substrate.

FIG. 2 depicts (not to scale) a typical first combinatorial library 50, which is comprised of discrete thin films 52 arrayed on a substrate 54. The library 50 shown in FIG. 2 comprises a 17-column by 17-row triangular array 56 of thin films 52, though the number of array elements (thin films 52) and their spatial distribution can vary. Normally, the thin films are about 0.1 microns to about 1.0 microns thick, and their surface areas vary from about 0.25 $mm^2$ to about 9 $mm^2$ in diameter. In addition, neighboring thin films are usually spaced apart by about 0.5 mm to about 3 mm. Typically, thin films are separated by a sufficient amount of space so that interdiffusion between library members cannot occur; however, it is also possible with this invention to use libraries without space between the members. There can be 10 or more, 20 or more, 50 or more or preferably 60 or more members in a library used in this invention. With a larger number of library members, the methodology will be faster paced.

Thin film arrays can be prepared using a number of known fabrication techniques. These include physical vapor deposition (PVD) with selective masking to control deposition pattern, composition, and film thickness of individual array elements. Useful PVD methods comprise single- and multiple-source electron beam evaporation, pulsed-laser deposition, and D.C. or radio frequency (rf) sputtering. Pulsed laser deposition and sputtering use, respectively, a high power excimer laser and magnetically confined plasma to ablate material from targets (sources) onto the substrate. Although multiple sources are normally processed sequentially, PVD methods can be adapted to deposit materials from multiple targets simultaneously. Simultaneous deposition from multiple sources, or co-deposition, increases overall deposition rate and improves chemical mixing. Co-pending U.S. patent application "The Combinatorial Synthesis of Novel Materials," Ser. No. 08/327,513 (WO 96/11878), provides details of useful thin film fabrication techniques and is incorporated herein by reference. Liquid dispensing techniques are also discussed therein, which may make useful thin films for use in this invention. Furthermore, U.S. patent application no. 09/156,827, filed Sep. 18, 1998 discloses sol-gel methods that may make useful thin films for use in this invention, and which is incorporated herein by reference. Moreover, as disclosed in these applications, the arrays useful in the present invention can take many different shapes and sizes, for example, with regard to the number of members in the library or array and the materials present as the members of the library or array.

Typically, the combinatorial library 50 is prepared using library design software (not shown) coupled to a computer-controlled deposition device and, optionally, a material handling robot. The library design software provides a graphical interface for choosing starting materials and for selecting a layout of the thin film array. After the user inputs synthesis parameters, the library design software calculates a recipe that describes the amount of starting materials for each of the thin films or array elements. In addition, the library design software displays a color-coded histogram that depicts the resulting library, and formats the recipe so that it is readable by computer modules that control the deposition device and the material handling robot, if present. In one embodiment of the library design software, the user may input synthesis parameters such as reaction temperature and pressure as functions of time, order and timing of the addition of starting materials, composition of gas atmosphere blanketing array elements during processing, and the like. In another embodiment, the user may input synthesis parameters in a separate software program that controls the deposition device. For a description of useful library design software, see U.S. patent application Ser. No. 09/174,856, filed Oct. 19, 1998, which is herein incorporated by reference.

Primary Screening

As discussed above and as shown in FIG. 1, primary screening 24 identifies library members that are semiconductors—that is, materials having a band gap, $E_g$, less than about 2 eV. The desired band gap of the material may limit the type of radiation useful for the method and apparatus of this invention. For materials having a band gap above about 1 eV, visible or ultraviolet radiation may be used, which may occur, for example, when researching oxides. However, designers of thermoelectric devices typically require that the material's band gap is approximately six to ten times its thermal energy, KT, where K is Boltzmann's constant ($8.6174 \times 10^{-5}$ $eVK^{-1}$). To satisfy this guideline, a device operating in a temperature range between 100 K and 1000 K, should have a narrower band gap that is roughly bounded as shown in expression II:

$$0.05 \text{ eV} \leq E_g \leq 0.9 \text{ eV} \qquad \text{II}$$

In terms of the wavelength, $\lambda$, of the excitation energy (heat or light) needed to promote an electron from a filled valence band to an empty conduction band, expression II can be rewritten as:

$$3 \times 10^1 \, \mu m \geq \lambda \geq 1 \, \mu m \qquad \text{III}$$

Expression III implies that any material that has a band gap that satisfies expression II, and is therefore potentially useful in a thermoelectric device, will absorb energy in the near and the far-infrared regions of the electromagnetic spectrum.

Primary screening 24 for a thermoelectric material thus comprises exposing members of the first combinatorial library to infrared radiation and selecting library members that absorb IR radiation having wavelengths satisfying expression III. Although there are many instruments and techniques for measuring IR absorption, fast Fourier transform infrared (FTIR) spectroscopy is particularly useful for primary screening 24. One embodiment employs an FTIR microscope spectrometer having a motorized stage for positioning the library relative to an IR source and detectors. During screening 24, the library (thin film array) is placed on the stage, and a computer, which controls the position of the stage, sequentially brings each of the library members in line with the IR source and detectors. In this way, IR absorption data are obtained for each of the library members in rapid serial fashion. Typically, a 150-member thin film array can be screened in about twenty minutes. Other useful infrared measurement techniques are described in co-pending U.S. patent application "Infrared Spectroscopy and Imaging of Libraries," Ser. No. 08/946,135, filed Oct. 7, 1997, which is herein incorporated by reference.

Primary Screening-IR Transparent Substrates

Figure 3:
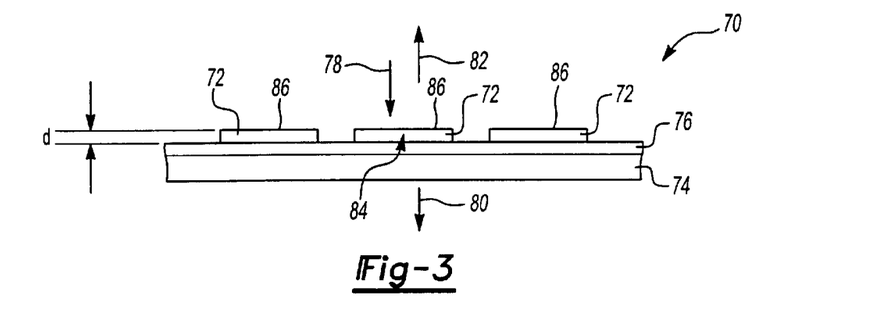
FIG. 3 is a cross sectional view of a portion of a first combinatorial library comprised of discrete thin films arrayed on an IR transparent substrate.

In primary screening 24, the methods employed to collect and analyze IR absorption data depend on whether the substrate that supports the thin films can transmit IR radiation. FIG. 3 is a cross sectional view of a portion of a first combinatorial library 70 (not to scale), which is comprised of discrete thin films 72 arrayed on an IR transparent substrate 74. Here, "IR transparent substrate" refers to substrate materials that will transmit at least some IR radiation over the range of wavelengths defined by expression III. Suitable substrate 74 materials include, but are not limited to $BaF_2$, $CaF_2$, $MgF_2$ and other metal halides, ZnSe, ZnS, $SiO_2$, $Si_3N_4$, $Al_2O_3$, silicon, and germanium. An optional, thin passivation layer 76 (about one micron thick) is sandwiched between the thin films 72 and the substrate 74 to help prevent interlayer diffusion during fabrication of the thin films 72. Useful passiviation layer 76 materials include, but are not limited to $Al_2O_3$ and $SiO_2$.

As shown schematically in FIG. 3, each of the thin films 72 are probed with IR radiation (first vector 78) to identify library members (thin films 72) having a band gap satisfying expression II. As depicted by second 80 and third 82 vectors, and by a star 84, each of the thin films 72 may, respectively, transmit, reflect, or absorb IR radiation. The fraction of IR radiation 78 transmitted 80 and reflected 82 by the thin films 72 are represented by transmittance, $T(\lambda)$, and reflectance, $R(\lambda)$, which for a particular sample depend on the wavelength, $\lambda$, of the incident IR radiation 78. Typically, $R(\lambda)$ and $T(\lambda)$ are expressed as percentages and can be measured by optical spectroscopy (e.g., FTIR spectroscopy).

Figure 4:
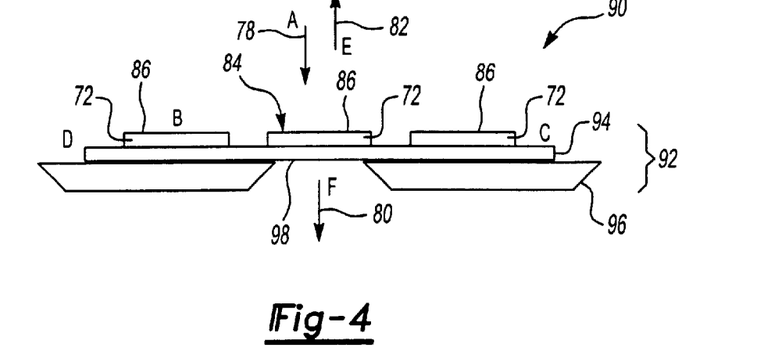
FIG. 4 is a cross sectional view of a portion of a second embodiment of a first combinatorial library.

FIG. 4 is a cross sectional view of a portion of a second embodiment of a first combinatorial library 90 (not to scale). Like the library 70 shown in FIG. 3, the second embodiment 90 comprises an array of discrete thin films 72. However, in the library 90 depicted in FIG. 4, the thin films 72 are arrayed on a substrate 92 comprised of a thin IR transparent membrane 94 that is interposed between the thin films 72 and a thicker support layer 96. The support layer 96 has a series of apertures 98 that are aligned with the thin films 72 so that any incident IR radiation 78 that is transmitted 80 through the thin films 72 can be detected on the support layer 96-side of the library 90. The membrane 94 is typically a few microns thick, and can be fabricated from a sheet of any material that can transmit at least some IR radiation over the range of wavelengths defined by expression III. Useful materials include $Si_3N_4$, high density polyethylene, mica, $Al_2O_3$, Ge, and $SiO_2$. Because it mainly provides mechanical support for the thin films 72, the support layer 96 can be fabricated from inexpensive materials—$SiO_2$, for example—which may or may not transmit light in the near and mid-infrared region of the electromagnetic spectrum.

Knowing the dependence of transmittance and reflectance on $\lambda$ allows measurement of the band gap, $E_g$, for each of the thin films 72 depicted in FIG. 3 and FIG. 4. During primary screening, the thin films 72 are scanned with IR radiation 78 over wavelengths that include at least a portion of the range specified by expression III. As described above, an FTIR microscope spectrometer or similar device can be used to measure $R(\lambda)$ and $T(\lambda)$. Typically, these measurements are made with IR radiation 78 striking the thin films 78 at an angle about normal to surfaces 86 of the thin films 72. Using theoretical models, $R(\lambda)$ and $T(\lambda)$ can be related to the dielectric response coefficient, $\epsilon(\lambda)$, which depends on absorption coefficient, $\alpha(\lambda)$, and index of refraction, $\eta(\lambda)$. See, C. Kittel, *Introduction to Solid State Physics*, 291–315 ($6^{th}$ ed. 1986), and R. Sehr and L. R. Testardi, *The Optical*

*Properties of p-Type Bi$_2$Te3—Sb$_2$Te$_3$ Alloys between 2–15 microns,* 23 *J. Phys. Chem. Solids* 1219, 1220–22 (1962), which are herein incorporated by reference. In particular, Sehr et al. provides expressions that can be used to calculate the absorption coefficient and the index of refraction from R(λ) (at normal incidence), T(λ), λ, and film thickness d:

$$T = \frac{(1-R)^2 e^{-\alpha d}}{1 - R^2 e^{-2\alpha d}} \qquad \text{IV}$$

$$R = \frac{(\eta-1)^2 + \left(\frac{\alpha \lambda}{4\pi}\right)^2}{(\eta+1)^2 + \left(\frac{\alpha \lambda}{4\pi}\right)^2} \qquad \text{V}$$

Figure 5:
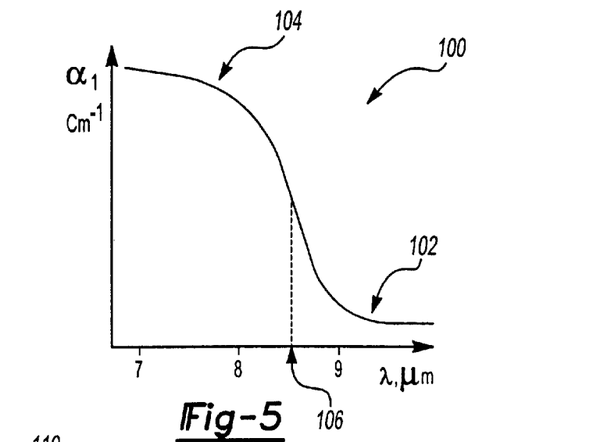
FIG. 5 shows a plot of absorption coefficient versus wavelength of incident IR radiation.

Thin films 72 that satisfy the screening criterion (expression II) will exhibit a dramatic increase in IR absorption when the excitation energy 78 exceeds the library member's band gap. This can be seen in FIG. 5, which nominally shows a plot 100 of absorption coefficient versus wavelength of incident IR radiation. In terms of λ, the value of the band gap is bounded below by an onset 102 of a steep rise in absorption coefficient at about 9 μm and is bounded above by a leveling off 104 of the absorption coefficient at about 8 μm. For screening purposes, it is usually sufficient to approximate the band gap by a narrow range of λ—a few microns or so—because the screening criterion based on λ (expression III) encompasses a relatively broad range of wavelengths. However, E$_g$ can be selected from other characteristics of the α vs. λ curve. For example, Sehr et al. suggests establishing E$_g$ from the value of λ at which the slope of the absorption coefficient is a maximum 106 (Moss' criterion). Whatever method is used, measurement of R(λ) and T(λ), and computation of α and E$_g$ are normally carried out using a computer system for data acquisition, data reduction, and control, which allows rapid and automatic screening of the combinatorial library.

Figure 6:
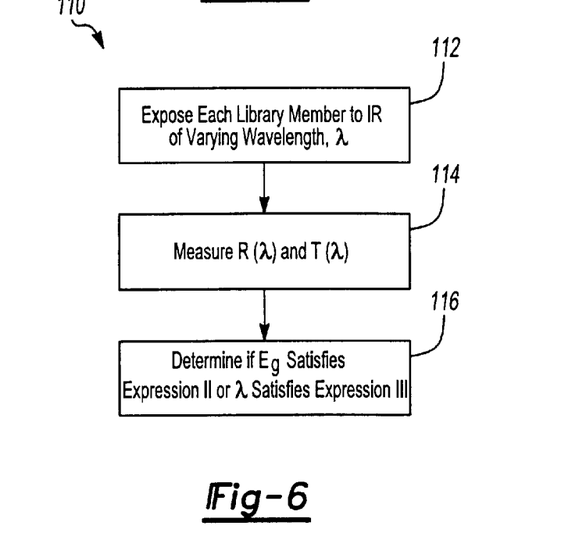
FIG. 6 summarizes primary screening for identifying semiconductors among members of a first combinatorial library arrayed on an IR transparent substrate.

FIG. 6 summarizes primary screening 110 for identifying semiconductors among members of a first combinatorial library arrayed on an IR transparent substrate. Primary screening 110 includes exposing 112 each of the library members to infrared radiation of varying wavelength, and measuring 114, as functions of wavelength, reflected and transmitted components of the infrared radiation, R(λ) and T(λ). Using R(λ) and T(λ), primary screening 110 includes determining 116 which library members, if any, have an optical band gap, E$_g$, satisfying the screening criterion defined by expression II. Using theoretical models for solid state absorption, reflection, and transmission of radiant energy, the absorption coefficient, α(λ), can be computed from measurements 114 of R(λ) and T(λ)—the onset of a substantial increase in α(λ) for some λ bounded by expression III indicates E$_g$ satisfies the screening criterion.

Primary Screening—IR Opaque Substrates

Figure 7:
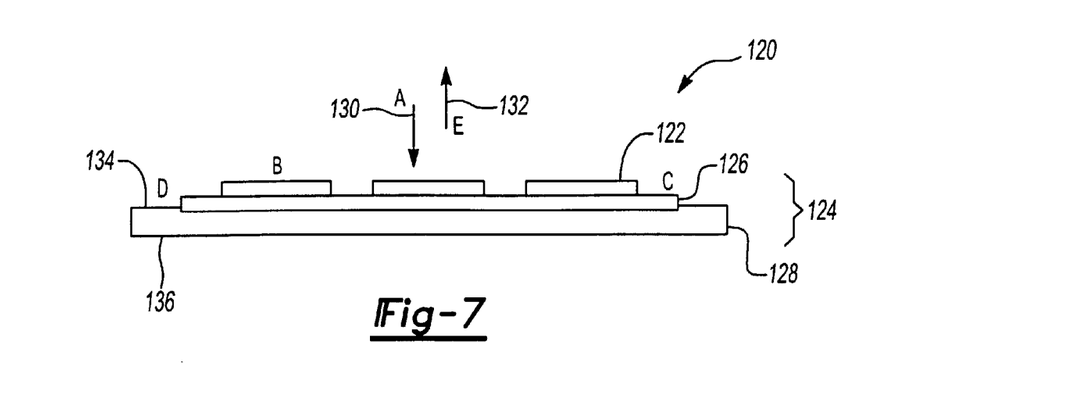
FIG. 7 shows a cross sectional view of a portion of a first combinatorial library comprised of discrete thin films arrayed on an IR opaque substrate.

FIG. 7 shows a cross sectional view of a portion of a first combinatorial library 120 (not to scale), which is comprised of discrete thin films 122 arrayed on an IR opaque substrate 124. Here, "IR opaque substrate" refers to substrate materials that will transmit little, if any, IR radiation over the range of wavelengths defined by expression III. The opaque substrate 124 shown in FIG. 7 is comprised of a relatively thin IR reflective layer 126 disposed on a relatively thick support layer 128 so that most of the incident IR radiation 130 passing through the thin films 122 reflects off the thin layer 126.

Although the substrate may consist of a single IR opaque layer, the use of a multi-layer substrate offers greater flexibility in library design. As depicted by a vector 132 directed away from the combinatorial library 120, most, if not all of the incident IR radiation 130 transmitted through the thin films 122 reflects off the IR reflective layer 126. One can make the thin layer 126 by coating, depositing, or laminating an IR-reflective material (typically a metal) on the support layer 128. To reduce interaction with the thin films 122 during library processing (heating, for example), the IR-reflective layer 126 is often made of tantalum, tungsten, or other refractory metals. Because the thicker support layer 128 mainly provides mechanical support for the thin films 122, it can be fabricated from inexpensive materials—SiO$_2$, for example—which may or may not transmit light in the near and mid-infrared region. If the support layer 128 readily transmits infrared radiation, the thin films 122 can be disposed directly on a top surface 134 of the support layer 128, and the IR reflective layer 126 can be disposed on a lower surface 136 of the support layer 128. This allows the use of an IR reflective layer 126 made of a material having a lower melting point than tantalum since the support layer 128 can be formulated to minimize interaction with the thin films 122 during heating.

The IR opaque substrate 124 prevents measurement of transmittance, which makes it difficult to determine the absorption coefficient or the band gap of each library member. However, since primary screening selects the most promising thermoelectric materials by eliminating non-semiconductors, it does not require absolute measurement of the absorption coefficient or the band gap. Instead, for each library member, primary screening need only detect the presence or absence of infrared absorption over at least a portion of the range of wavelengths defined by expression III. In this way, primary screening discerns trends in semiconductor phase formation as a function of library member composition.

Figure 8:
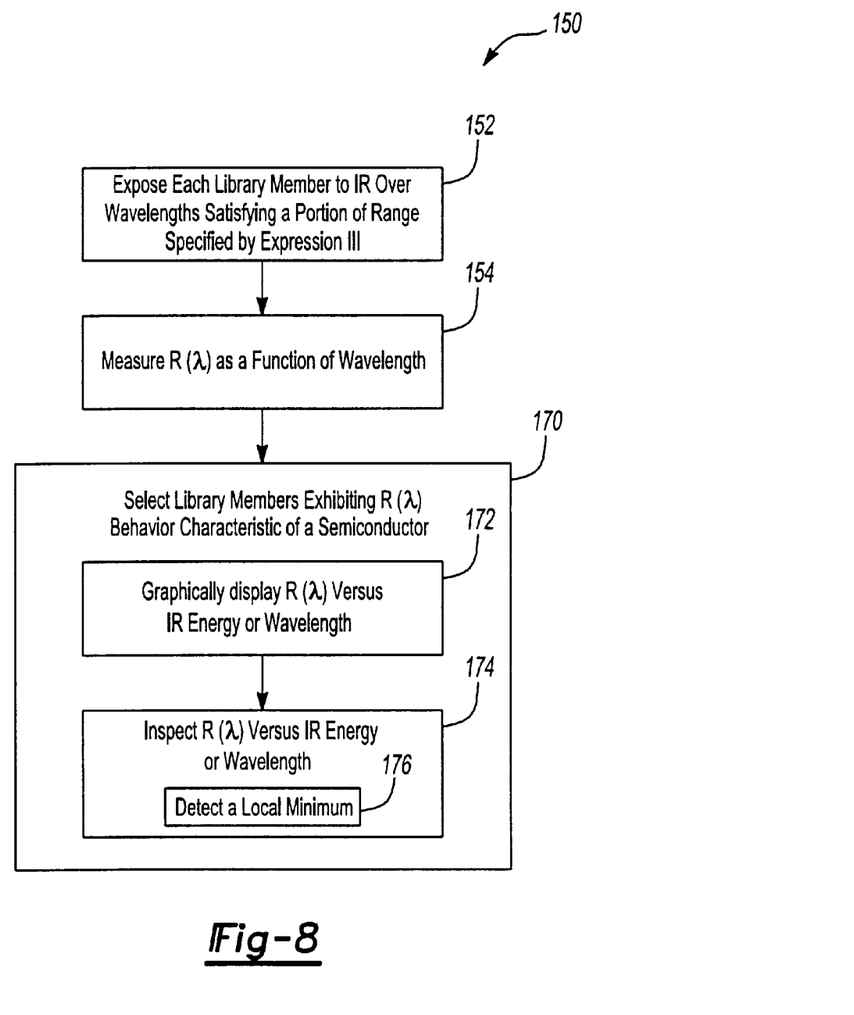
FIG. 8 summarizes primary screening of members of a first combinatorial library arrayed on an IR opaque substrate.

FIG. 8 summarizes primary screening 150 of members of a first combinatorial library arrayed on an IR opaque substrate. Primary screening 150 includes exposing 152 each library member to IR radiation over wavelengths that include at least a portion of the range specified by expression III, and measuring 154 the amount of IR radiation reflected by each of the library members, R(λ). As described above, an FTIR microscope spectrometer or similar device can be used to measure R(λ).

Typically, R(λ) is expressed as a fraction of the amount of IR radiation that reflects directly off the reflective layer 126 of FIG. 7. Thus, a library element or thin film with a high reflectivity in the infrared region of the electromagnetic spectrum—a metal, for example—will reflect the incident IR radiation 130 at approximately the same efficiency as the reflective layer 126 (i.e., baseline signal), resulting in a reflectance of about 1.0. For highly reflective thin films 122, slight variations in R(λ) from unity result from differences in electrical conductivity between the thin films 122 and the reflective layer 126, but such differences typically contribute ten percent or less to measured reflectance. Similarly, thin films 122 having band gaps falling above the range defined by expression II, are transparent to near and mid-infrared radiation, and therefore exhibit a reflectance of about 1.0.

Figure 9:
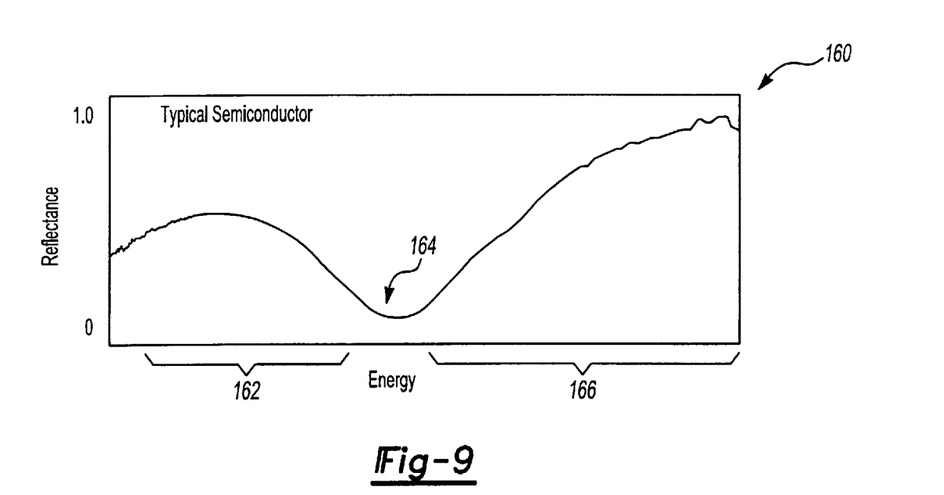
FIG. 9 is a plot of reflectance versus energy of incident IR radiation for a typical semiconductor on an IR opaque substrate.

Thin films 122 that are semiconductors and possess band gaps falling within the range defined by expression II, will absorb some of the incident IR radiation 130, resulting in R(λ) less than 1.0. This behavior can be seen in FIG. 9, which is a plot 160 of reflectance versus energy of incident IR radiation 130 for a typical semiconductor. At lower energy levels 162 (longer wavelengths), reflectance drops with increasing energy as the semiconductor absorbs IR radiation. This continues until the reflectance versus energy curve reaches a minimum 164. At higher energy levels 166, reflectance rises with increasing energy as the semiconductor becomes more transparent. As shown in FIG. 9, reflectance continues to rise with increasing energy until it is about unity, indicating that the incident IR radiation 130 is probing the reflective layer 126. Thus, a semiconducting member of the first combinatorial library of materials 120 exhibits a local minimum in reflectance when scanned with infrared radiation over energy levels or wavelengths satisfying expression II or III, respectively.

Referring again to FIGS. 7 and 8, primary screening 150 also includes selecting 170 library members exhibiting R(λ) characteristic of a semiconductor. Selection 170 of library members typically graphically displaying 172 reflectance of the thin films 122 versus incident IR energy or wavelength, and inspecting 174 each of the reflectance versus energy curves to select library members having curves characteristic of semiconductors. In particular, inspection 174 often comprises detecting 176 a local minimum in the reflectance versus energy (wavelength) curve to select semiconducting members of the first combinatorial library of materials 120.

Figure 10:
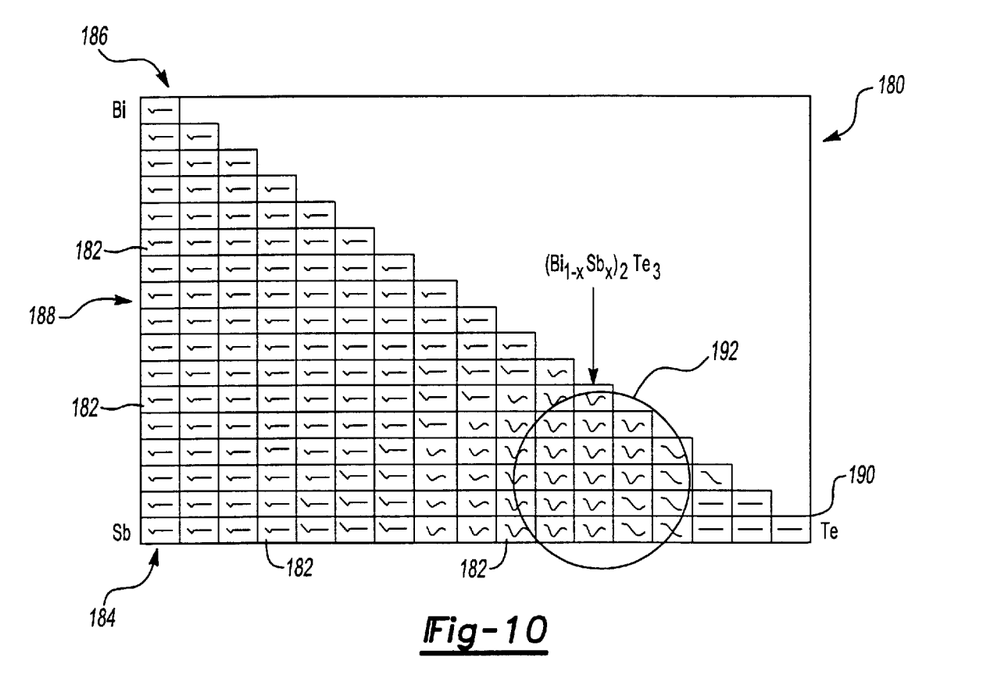
FIG. 10 shows a triangular array of reflectance versus energy curves for a combinatorial library comprised of mixtures of bismuth, antimony, and tellurium.

For example, FIG. 10 shows a triangular array 180 of reflectance versus energy curves 182 for a combinatorial library comprised of mixtures of bismuth, antimony, and tellurium. Each of the curves 182 corresponds to library members having different molar fractions of Bi, Sb, and Te. Generally, the fraction of bismuth in library members increases from bottom 184 to top 186 of the array 180, and the fraction of tellurium in library members increases from left 188 to right 190 of the array 180. In addition, the fraction of antimony in library members generally increases from top 186 to bottom 184 and from right 190 to left 188 of the array 180.

The curves 182 shown in FIG. 10 were obtained using infrared reflectance spectroscopy. Library members that are semiconductors have $E_g$ satisfying expression II; they absorb IR radiation at wavelengths defined by expression III, and have reflectance versus energy curves 182 that exhibit a local minimum. Library members that have $E_g$>0.9 eV reflect most of the incident IR radiation throughout the range of wavelengths defined by expression III, and therefore have reflectance versus energy curves that are generally flat. A highlighted region 192 of the triangular array 180 identifies semiconductors having compositions $(Bi_{1-x}Sb_x)_2Te_3$ for $0 \leq x \leq 1$.

Isolating Single-Phase Semiconductors

Phase Identification and Purification

As described in the previous section and with reference to FIG. 1, primary screening 24 eliminates library members that are not semiconductors. Since primary screening 24 does not distinguish between single-phase and multiple-phase semiconductors, the method 20 includes isolating 26 single-phase semiconductors from among library members identified by primary screening 24. Thus, the primary screening, screens for semi-conductors.

The method 20 includes an isolating step 26 because a phase exhibiting a low figure of merit, ZT, in a multiphase material can mask another phase exhibiting higher ZT. For example, a library member comprised of magnesium, copper, and tellurium, may consist of three phases: a Mg—Cu—Te alloy, unalloyed copper, and unalloyed magnesium. Because Cu and Mg are far more electrically conductive than the Mg—Cu—Te alloy, values of the library member's Seebeck coefficient, S, and resistivity, ρ, will be representative of the more conductive copper and magnesium phases, and not of the Mg—Cu—Te phase. Since ZT depends on S and ρ, the presence of additional phases or impurities—Cu and Mg in this example—can depress ZT, resulting in a "false negative" during secondary screening 30.

Figure 11:
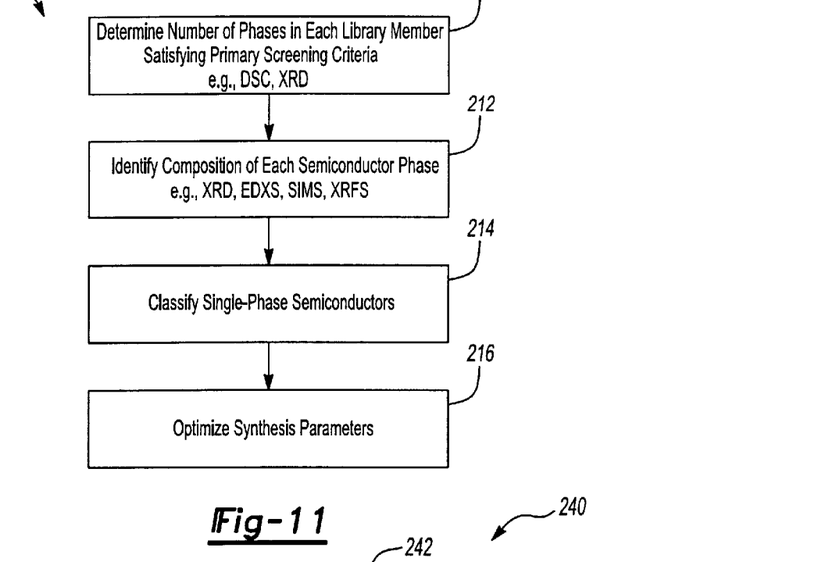
FIG. 11 shows details of techniques to isolate single-phase materials following primary screening.

As shown in FIG. 11, which provides details of the isolation step 26, the method 20 of FIG. 1 can use many techniques to isolate 26 single-phase materials. The isolation step 26 includes determining 210 the number of phases present in a particular library member, using techniques such as differential scanning calorimetry (DSC), scanning x-ray diffraction (XRD), and the like. In addition, the isolation step 26 can include identifying 212 the composition of each of the semiconductor phases, using techniques such as energy dispersive x-ray spectroscopy (EDXS), secondary ion mass spectrometry (SIMS), x-ray fluorescence spectroscopy (XRFS), and so on. Some of the isolation 26 techniques can determine 210 the number of phases present and identify 212 the compositions of each phase. For example, one can use XRD to obtain a characteristic spectrum or "fingerprint" of a library member. Using software, one can then search a computer database of spectra to match the characteristic spectrum with a spectrum of known material composition.

Following identification of single-phase semiconductors, the isolation step 26 may include classifying 214 single-phase semiconductors into three general categories: known thermoelectric materials, known materials having unknown thermoelectric properties, and new materials. Usually, only new materials and known materials having unknown thermoelectric properties undergo further investigation. In this way, primary screening 24 and the isolation 26 of single-phase materials substantially reduce the number of library members under investigation.

The isolating step 26 may also include optimizing 216 synthesis parameters to make single-phase materials. Thus, for example, one may use parallel or rapid serial differential scanning calorimetry to examine phase formation in response to changes in reaction conditions, such as synthesis temperature, anneal duration, reactant addition sequence, gas composition, and so on. For a description of a useful parallel DSC, see, e.g., U.S. patent application Ser. No. 09/210,485, filed Dec. 11, 1998, which is herein incorporated by reference.

Secondary Screening—Determination of the Thermoelectric Figure of Merit

As shown in FIG. 1, the method 20 includes secondary screening 30—determination of the thermoelectric figure of merit, or a quantity related to ZT—of each member of a second combinatorial library of materials. Secondary screening 30 selects a subset of library members with largest ZT, and presumably, highest thermoelectric performance. The second combinatorial library of materials comprises at least a portion of single-phase semiconductors from the isolating step 26 of the method 20. Ordinarily, members of the second combinatorial library comprise either new materials or previously discovered materials having unknown thermoelectric properties.

Secondary screening 30 can be understood by referring to FIG. 12, which is a schematic diagram of a model thermoelectric device 240, and as discussed below, represents a single member of a second combinatorial library. The thermoelectric device 240 includes a thermoelectric material 242 connected to a voltage source 244 through a pair of electrically conductive wires 246. When the voltage source 244 applies an electrical potential across first 248 and second 250 contacts, heat flows from one contact to the other through the thermoelectric material 242. As discussed in the background of the invention, this phenomenon is called the Peltier effect. At steady state or under adiabatic conditions, the applied electrical potential will pump heat equal to the heat carried by thermal conduction, which leads to an alternate expression for the thermoelectric figure of merit:

$$ZT = \frac{Q_P}{Q_J} = \frac{P_P}{P_J} \qquad \text{VI}$$

In equation VI, $Q_P$ and $Q_J$ are the amount of heat transported by the Peltier effect and the amount of energy lost to Joule heating, respectively; $P_P$ and $P_J$ are power losses corresponding to the Peltier effect and Joule heating. For a more detailed discussion of equation VI, see T. Tritt, 478 Materials Research Society Symposium Proceedings at 34 (1997), which is herein incorporated by reference.

The total power, P, dissipated by the device 240 is the sum of the power losses due to the Peltier effect and Joule heating:

$$P = P_J + P_P = \frac{V^2}{R} + \Pi \frac{V}{R} \qquad \text{VII}$$

In equation VII, the first term on the right hand side of the expression is the power dissipated by Joule heating, $P_J$, and the second term is the power dissipated by the Peltier effect, $P_P$. In addition, R is the electrical resistance of the device 240, Π is the Peltier coefficent of the thermoelectric material 242 measured relative to the contacts 248, 250, and V is the applied electrical potential. Significantly, the Joule heating component of the power dissipated by the device 240 depends on the square of the applied voltage, whereas the Peltier component of the power dissipated by the device 240 depends linearly on V.

This difference in V dependence allows one to determine $P_J$ and $P_P$ from time-dependent measurements of power dissipation at interfaces between the contacts 248, 250 and the thermoelectric material 242. When the voltage source 244 applies an oscillatory electrical potential across the contacts 248, 250—$V_0 \cos(\omega_0 t)$, for example—$P_J$ will oscillate at twice the reference frequency, $\omega_0$, because the applied voltage is squared in the Joule heating component of power dissipation. In contrast, $P_P$ will oscillate at $\omega_0$ because V is linear in the Peltier component of power dissipation. By measuring power dissipated at the contacts 248, 250 as a function of time, P(t), and by transforming power from the time domain to the frequency domain, P(t)→P(ω), one can obtain $P_P$ and $P_J$ from the power versus frequency spectrum since $P_P = P(\omega_0)$ and $P_J = P(2\omega_0)$.

Figure 13:
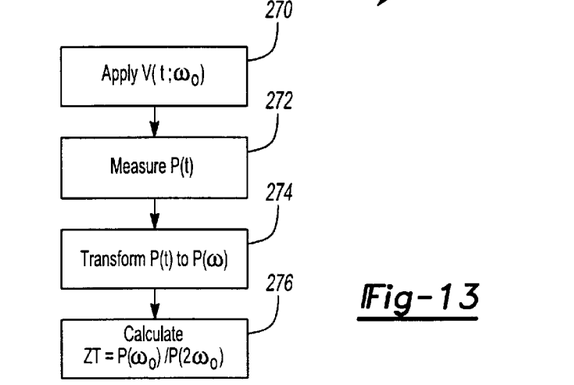
FIG. 13 depicts secondary screening.

Thus, as shown in FIG. 13, which depicts secondary screening 30, ZT is determined by applying 270 an oscillatory voltage, V(t), having a reference frequency, $\omega_0$, across at least one member of a second combinatorial library of materials. Secondary screening 30 includes measuring 272 power as a function of time, P(t), dissipated by the at least one member of the second combinatorial library while applying V(t). To extract $P_P$ and $P_J$ from measurements of power dissipation, secondary screening 30 includes transforming 274 power as a function of time, P(t), to power as a function of frequency, P(ω). Finally, secondary screening 30 includes calculating 276 ZT from the power versus frequency spectrum and equation VI:

$$ZT = \frac{P(\omega_0)}{P(2\omega_0)} \qquad \text{VIII}$$

In equation VIII, $P(\omega_0)$ and $P(2\omega_0)$ are amplitudes of the power at the reference frequency and at two times the reference frequency, respectively.

For each library member, ZT depends on measurement 272 of P(t). Electrical power loss from an individual library member appears as infrared emission or heat evolution, which can be measured 272 with infrared imaging devices such as bolometers, focal plane arrays, or photodiodes. In addition, heat evolution at interfaces 280 between the first 248 or second contacts 250 and thermoelectric material 242 of the device 240 (individual library member) shown in FIG. 12, can be measured using conventional temperature sensing devices such as thermocouples, thermistors, or resistance thermometric devices (RTDs). Infrared imaging using a focal plane array detector is especially useful because it allows for parallel measurement of all elements of a library.

Figure 12:
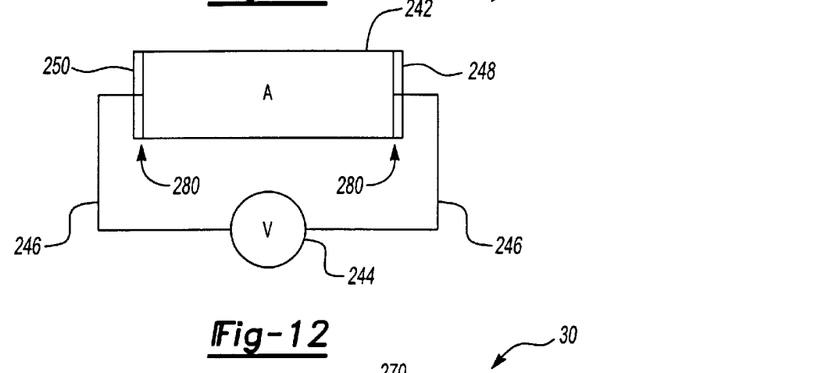
FIG. 12 is a schematic diagram of a model thermoelectric device, which represents a single member of a second combinatorial library.
Figure 14:
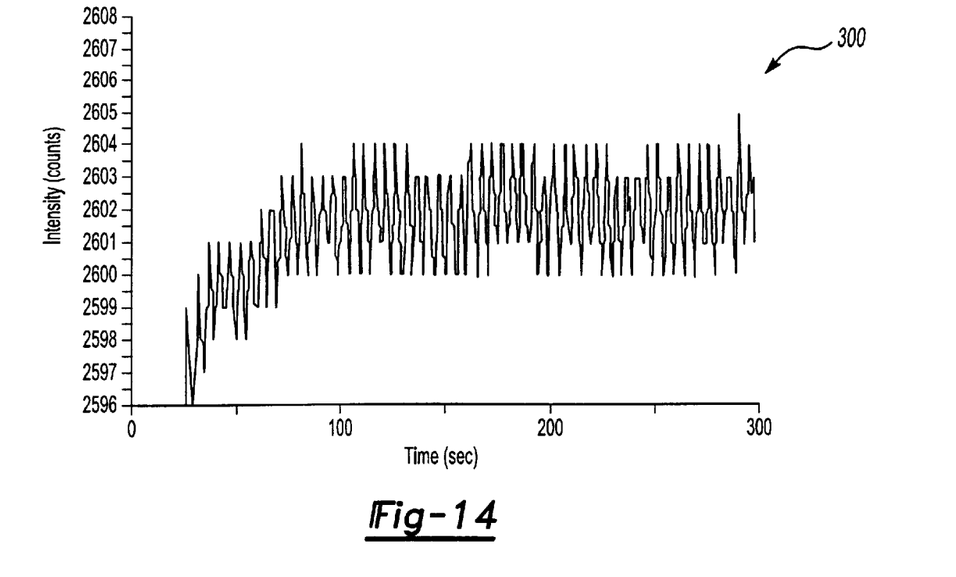
FIG. 14 is a plot of infrared emission intensity versus time during application of a sinusoidal voltage across a library member or thermoelectric device of the type shown in FIG. 12.
Figure 15:
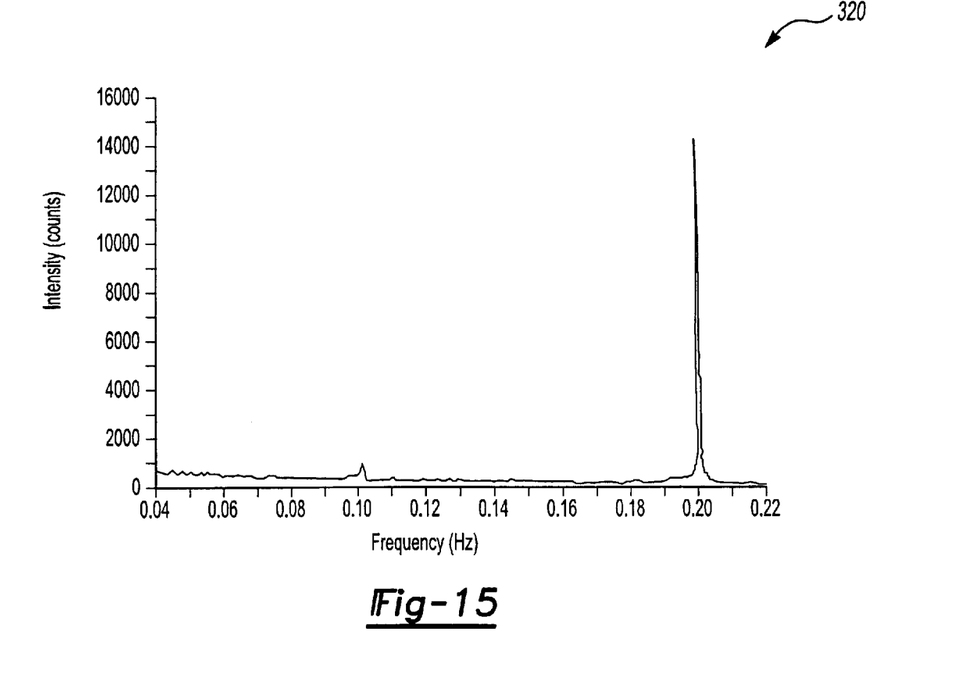
FIG. 15 is a plot of IR emission intensity versus frequency calculated from data of FIG. 14 using a computer-implemented Fast Fourier Transform (FFT).

FIG. 14 is a plot 300 of infrared emission intensity versus time during application of a sinusoidal voltage across a library member or thermoelectric device of the type shown in FIG. 12. FIG. 15 is a corresponding plot 320 of IR emission intensity versus frequency calculated from data of FIG. 14 using a computer-implemented Fast Fourier Transform (FFT). The FFT computer program is based on the algorithm described in W. H. Press et al., Numerical Recipes in C, 584–91 (2d ed. 1997), which is herein incorporated by reference. As can be seen by the plot 320 of IR emission intensity versus frequency, the applied sinusoidal voltage has a reference frequency, $\omega_0$, equal to 0.1 Hz, and a figure of merit equal to about 0.1 since $$ZT = \frac{\text{IR emission intensity at } \omega = \omega_0 = 0.1 \text{ Hz}}{\text{IR emission intensity at } \omega = 2\omega_0 = 0.2 \text{ Hz}} \qquad \text{IX}$$

One can rapidly measure ZT for each library member by parallel measurement of IR emission intensity versus time using an infrared camera coupled with image analysis computer software. A useful thermal imaging analysis program is described in PCT/US99/07358, filed Apr. 1, 1999, which is herein incorporated by reference.

Figure 16:
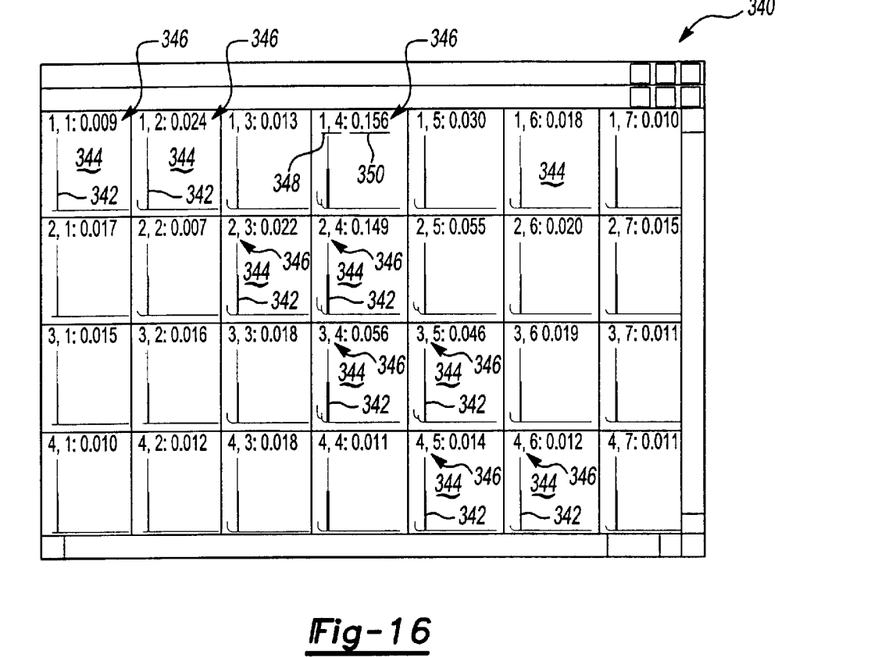
FIG. 16 shows a representative data set from a thermal imaging analysis program.

FIG. 16 shows a representative data set from a thermal imaging analysis program. The data were obtained from IR imaging of a 7-by-7 array of thermoelectric devices or second combinatorial library of materials. FIG. 16 is graphical output 340 from the thermal imaging analysis program. Plots 342 of IR emission intensity versus time for each array element (thermoelectric device) are displayed in individual windows 344. Text 346 in the upper left-hand corner of each of the windows 344 lists an array element index 348 (row, column) and measured ZT 350.

Preparation of a Second Combinatorial Library of Materials

Figure 17:
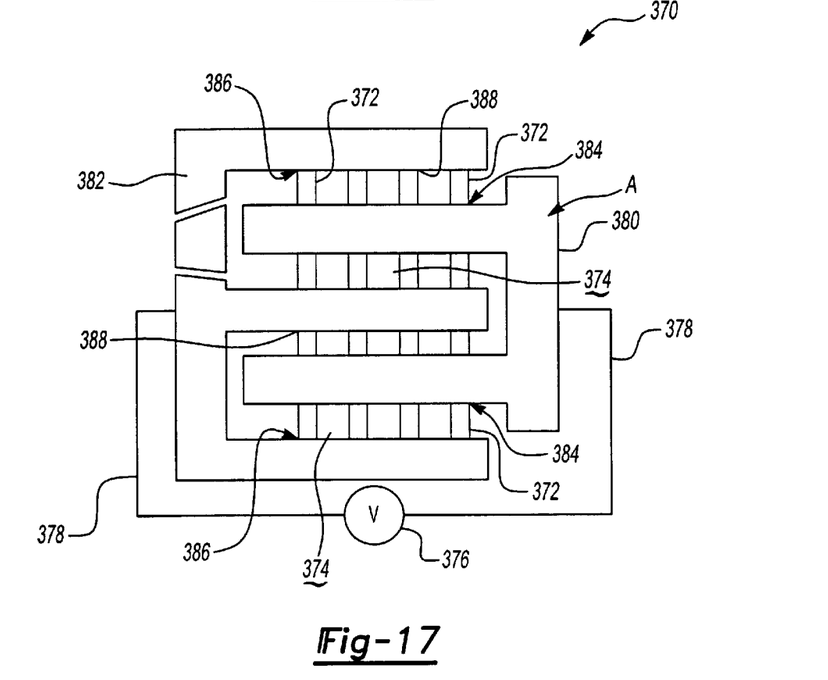
FIG. 17 depicts a second combinatorial library comprised of discrete thin films or thermoelectric materials arrayed on a non-electrically conductive substrate.

FIG. 17 depicts (not to scale) a second combinatorial library 370, which is comprised of discrete thin films 372 or thermoelectric materials arrayed on a non-electrically conductive substrate 374. The library 370 shown in FIG. 17 comprises a four-column by four-row array 376 of thin films 372, though the number of array elements (thin films) and their spatial distribution can vary. The library 370 can be prepared using the same techniques used to fabricate the first combinatorial library of materials 50, 70, 90 shown in FIGS. 2–4. Such techniques include single- and multiple-source physical vapor deposition (PVD) with selective masking to control deposition pattern, composition, and film thickness of individual array elements. In addition, the second combinatorial library 370 is typically prepared using, library design software coupled to computer-controlled deposition devices and material handling robots as discussed earlier.

As shown in FIG. 17, each of the thin films 372 are connected in parallel to a voltage source 376 through a pair of electrically conductive wires 378 and first 380 and second 382 contacts. Each of the thin films 372 has a first end 384 and a second end 386. The first 384 and second 386 ends of each of the thin films 372 contact, respectively, the first 380 and second 382 contacts. As a result, when the voltage source 376 applies an oscillatory electrical potential between the first 380 and the second 382 contacts, heat flows from one contact to the other through each of the thin films 372 simultaneously. As discussed above in reference to FIG. 13, during application of the electrical potential, power is dissipated at interfaces 388 between the contacts 380, 382 and each of the thin films 372, which can be resolved into $P_P$ and $P_J$—power losses due to the Peltier effect and Joule heating, respectively. Equation VI, which relates $P_P$ and $P_J$ to the thermoelectric figure of merit, assumes that no heat is lost to the substrate 374, and that either no heat is lost to the volume surrounding the library 370, or that heat losses to the surroundings are at steady state. Therefore, the substrate 374 is typically a thin sheet—25 to 50 microns thick, for example—fabricated from a material having low thermal conductivity. Useful substrate 374 materials include conventional polymeric electrical insulation, such as filled or unfilled polyimide, polyisocyanurate, polystyrene, polyethylene, melamine, poly(vinyl chloride), polybenzimidazole, polypyrone, polyurea, polyphenylquinoxaline, phenolic resin, and the like.

To minimize heat conduction and convection losses from each of the thin films 372, the library 370 generally undergoes secondary screening while exposed to vacuum. In addition, the applied voltage is kept as small as possible, and the reference frequency, $\omega_0$ is typically maintained at 0.1 Hz or less. To ensure good electrical contact, the first 380 and second 382 contacts are often made of a high conductivity metal such as silver, gold, chromium, tantalum or copper. In addition, the use of high conductivity metal contacts 380, 382 improves the resolution of $P_P$ and $P_J$ since such metals have a low Peltier coefficient relative to semiconductors. See equation VII.

Alternate Secondary Screening Method—
Measurement of N/m*

Figure 18:
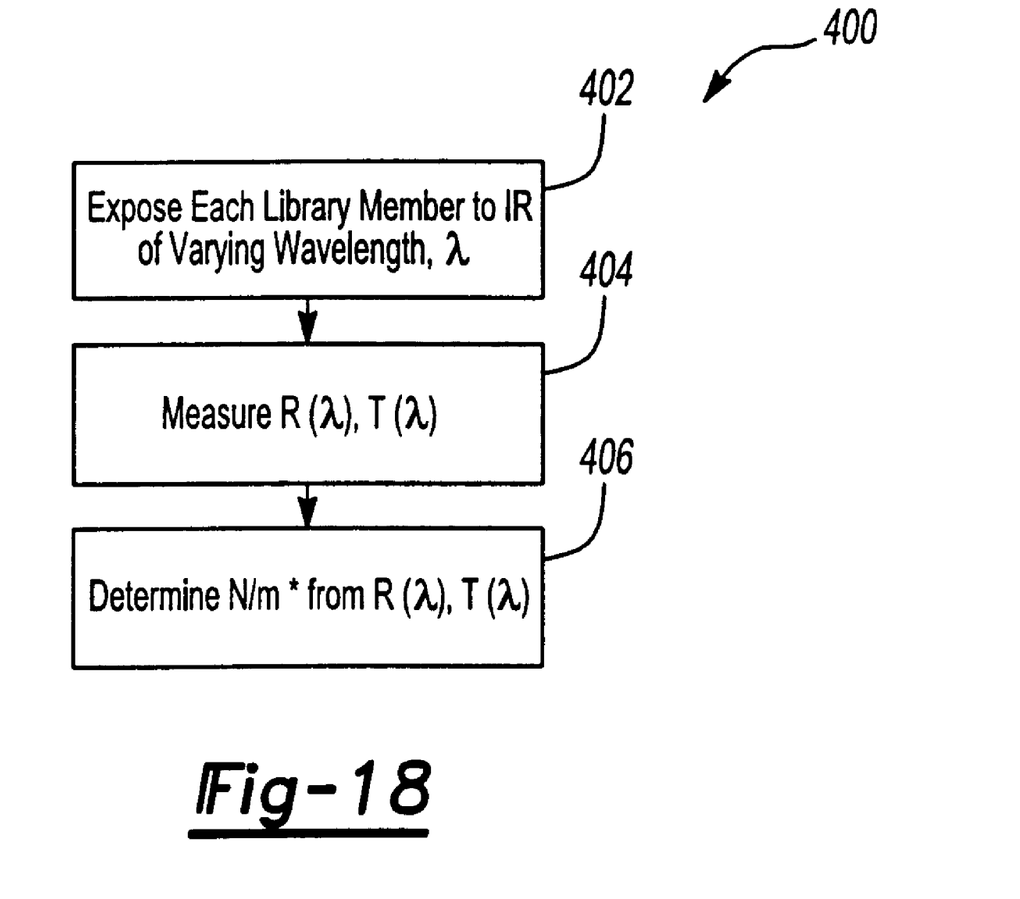
FIG. 18 illustrates an alternate secondary screening method, which is based on measurement and optimization of N/m*, the ratio of charge carrier density to quasiparticle effective mass.

FIG. 18 illustrates an alternate secondary screening 400 method, which is based on measurement and optimization of N/m*, the ratio of charge carrier density to quasiparticle effective mass. Because the quasiparticle effective mass relates to the Seebeck coefficient, S, and the charge carrier density is a fundamental component of electrical conductivity, $\rho^{-1}$, and because ZT depends on S and $\rho$, optimizing N/m* can lead to discovery of improved thermoelectric materials. For a discussion of N and m* and how they relate to S and $\rho^{-1}$, see See C. Kittel, *Introduction to Solid State Physics* at 142, 214 ($6^{th}$ ed. 1986).

As shown in FIG. 18, the method 400 comprises exposing 402 members of a second combinatorial library of materials to infrared radiation of varying wavelength, measuring 404 reflected and transmitted components of the incident infrared radiationas functions of wavelength, and determining N/m* 406 from measurements of $R(\lambda)$ and $T(\lambda)$. As in primary screening 24 shown in FIG. 1, members of the second combinatorial library are exposed to IR radiation having wavelengths that satisfy expression III. Likewise, $R(\lambda)$ and $T(\lambda)$ can be measured for each library member using optical spectroscopy methods (e.g. FTIR spectroscopy) described in connection with primary screening 24.

The second combinatorial library can be prepared using the same techniques used to fabricate the first combinatorial library of materials 50, 70, 90 shown in FIGS. 2–4. Generally, the second combinatorial library comprises at least a portion of single-phase semiconductors from the isolating step 26 of the method 20 shown in FIG. 1. Ordinarily, members of the second combinatorial library comprise either new materials or previously discovered materials having unknown thermoelectric properties.

Referring again to FIG. 18, the method 400 uses mathematical models that describe optical and electronic behavior of thermoelectric materials to determine 406 N/m*. One useful expression for dielectric response coefficient, $\epsilon(\lambda)$, relates N/m* to measurements of the index of refraction, $\eta$, and the absorption coefficient, $\alpha$:

$$\varepsilon(\lambda) = \eta^2 - \left(\frac{\alpha\lambda}{4\pi}\right)^2 = \varepsilon_i - \frac{1}{\varepsilon_0}\left(\frac{e\lambda}{2\pi c}\right)^2 \frac{N}{m^*} \qquad \text{X}$$

In equation X, $\epsilon_i$ is the dielectric coefficient for a library member in the absence of charge carriers; $\epsilon_0$, c and e are fundamental constants, and are respectively, the dielectric coefficient of free space, the speed of light in a vacuum, and the electronic charge. For a more complete discussion of equation X, see R. Sehr and L. R. Testardi, 23 *J. Phys. Chem. Solids* at 1220 (1962).

Using equation X, one can calculate N/m* for each library member knowing $\eta$ and $\alpha$ dependence on the wavelength of incident IR radiation, $\lambda$. As described in an earlier section on optical measurements of band gap, $\eta$ and $\alpha$ can be calculated from measurements of $R(\lambda)$ and $T(\lambda)$ using equations IV and V. Once $\eta$ and $\alpha$ are known for a given library member, N/m* can be determined from equation X. For example, a plot of $\epsilon(\lambda)$ versus $\lambda^2$ should yield a straight line having a slope that is proportional to N/m*.

The above description is intended to be illustrative and not restrictive. Many embodiments and many applications besides the examples provided will be apparent to those of skill in the art upon reading the above description. The scope of the invention should therefore be determined, not with reference to the above description, but should instead be determined with reference to the appended claims, along with the full scope of equivalents to which such claims are entitled. Although elements of the invention are described in terms of software, the invention may be implemented in software or hardware or firmware, or any combination of the three. In addition, the steps of the invention can be performed in a different order and still achieve desirable results. The disclosures of all articles and references, including patent applications and publications, are incorporated by reference for all purposes.

What is claimed is:

1. A method for screening combinatorial libraries of semiconductor candidate materials comprising:
   providing a combinatorial library of at least 10 thin film semiconductor candidate materials on a common substrate,
      wherein individual members of the library are different and span a range of compositions, wherein the individual members each are provided on a substrate as a thin film of about 0.1 to 1.0 micron thick, with a surface area of about 0.25 mm² to about 9 mm², and wherein the individual members are separated from each other on the substrate to avoid interdiffusion between library members;

screening the combinatorial library by exposing the combinatorial library to infrared radiation of varying wavelength, including measuring the amount of infrared radiation, $R(\lambda)$, reflected from each of the members of the combinatorial library of materials as a function of the wavelength, wherein $R(\lambda)$ is measured relative to a baseline of reflected infrared radiation;

identifying semiconducting members of the combinatorial library of materials that exhibits $R(\lambda)$ of less than 1.0 and absorb infrared radiation within a wavelength range of about $3 \times 10^1$ μm to about 1 μm; and preparing identified library members for additional screening based upon the results of said identifying step.

2. The method of claim 1, wherein the identifying step includes:

graphically displaying $R(\lambda)$ versus wavelength or energy; and detecting a local minimum in $R(\lambda)$ that is less than about fifty percent of the baseline of reflected infrared radiation.

3. The method of claim 1, wherein the screening is performed in serial fashion.

4. The method of claim 1, wherein the members of the combinatorial library of materials are deposited on the substrate using pulsed laser deposition or magnetron sputtering.

5. The method of claim 1, further comprising determining a thermoelectric figure of merit for each member of the library.

6. The method of claim 1, further comprising making bulk samples of at least one identified library member.

* * * * *